United States Patent
Cohen et al.

(10) Patent No.: US 8,110,349 B2
(45) Date of Patent: Feb. 7, 2012

(54) METHOD FOR PRODUCING BIOMOLECULE DIAGNOSTIC DEVICES

(75) Inventors: David Cohen, San Bruno, CA (US); Rosann Kaylor, Cumming, GA (US); Curtis Sayre, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/853,776

(22) Filed: Aug. 10, 2010

(65) Prior Publication Data

US 2011/0086161 A1    Apr. 14, 2011

Related U.S. Application Data

(62) Division of application No. 10/139,025, filed on May 3, 2002, now Pat. No. 7,771,922.

(51) Int. Cl.
*C12Q 1/00* (2006.01)

(52) U.S. Cl. ... 435/4; 435/283.1; 435/287.1; 435/287.2; 435/288.3; 435/7.1; 422/50; 422/68.1; 422/82.11

(58) Field of Classification Search .......... 435/4, 283.1, 435/287.1, 287.2, 288.3, 7.1; 422/50, 61, 422/68.1, 82.11
See application file for complete search history.

(56) References Cited

U.S. PATENT DOCUMENTS

| | | |
|---|---|---|
| 3,641,354 A | 2/1972 | De Ment |
| 4,011,009 A | 3/1977 | Lama et al. |
| 4,274,706 A | 6/1981 | Tangonan |
| 4,312,228 A | 1/1982 | Wohltjen |
| 4,330,175 A | 5/1982 | Fujii et al. |
| 4,363,874 A | 12/1982 | Greenquist |
| 4,399,686 A | 8/1983 | Kindlund et al. |
| 4,416,505 A | 11/1983 | Dickson |
| 4,442,204 A | 4/1984 | Greenquist et al. |
| 4,477,158 A | 10/1984 | Pollock et al. |
| 4,480,042 A | 10/1984 | Craig et al. |
| 4,528,260 A | 7/1985 | Kane |
| 4,534,356 A | 8/1985 | Papadakis |
| 4,537,861 A | 8/1985 | Elings et al. |
| 4,552,458 A | 11/1985 | Lowne |
| 4,561,286 A | 12/1985 | Sekler et al. |
| 4,562,157 A | 12/1985 | Lowe et al. |
| 4,587,213 A | 5/1986 | Malecki |
| 4,596,697 A | 6/1986 | Ballato |

(Continued)

FOREIGN PATENT DOCUMENTS

EP    0205698 A1    12/1986

(Continued)

OTHER PUBLICATIONS

Pritchard et al., Micron Scale Patterning of Biological Molecules, 1995, Angew Chem Int Ed Engl, vol. 34, No. 5, pp. 91-93.*

(Continued)

*Primary Examiner* — Melanie J Yu
(74) *Attorney, Agent, or Firm* — Dority & Manning, P.A.

(57) ABSTRACT

A biosensor includes a substrate member with a pattern of active areas of receptive material and a pattern of blocking material layers. The receptive material and blocking material are attached to the substrate member with a photo-reactive crosslinking agent activated in a masking process. The receptive material is specific for an analyte of interest.

12 Claims, 1 Drawing Sheet

U.S. PATENT DOCUMENTS

| | | | |
|---|---|---|---|
| 4,614,723 A | 9/1986 | Schmidt et al. | |
| 4,632,559 A | 12/1986 | Brunsting | |
| 4,647,544 A * | 3/1987 | Nicoli et al. | 436/518 |
| 4,661,235 A | 4/1987 | Krull et al. | |
| 4,690,715 A | 9/1987 | Allara et al. | |
| 4,698,262 A | 10/1987 | Schwartz et al. | |
| 4,776,944 A | 10/1988 | Janata et al. | |
| 4,812,221 A | 3/1989 | Madou et al. | |
| 4,815,843 A | 3/1989 | Tiefenthaler et al. | |
| 4,818,710 A | 4/1989 | Sutherland et al. | |
| 4,837,715 A | 6/1989 | Ungpiyakul et al. | |
| 4,842,633 A | 6/1989 | Kuribayashi et al. | |
| 4,842,783 A | 6/1989 | Blaylock | |
| 4,844,613 A | 7/1989 | Batchelder et al. | |
| 4,851,816 A | 7/1989 | Macias et al. | |
| 4,876,208 A | 10/1989 | Gustafson et al. | |
| 4,877,747 A | 10/1989 | Stewart | |
| 4,895,017 A | 1/1990 | Pyke et al. | |
| 4,917,503 A | 4/1990 | Bhattacharjee | |
| 4,992,385 A | 2/1991 | Godfrey | |
| 4,999,489 A | 3/1991 | Huggins | |
| RE33,581 E | 4/1991 | Nicoli et al. | |
| 5,023,053 A | 6/1991 | Finlan | |
| 5,035,863 A | 7/1991 | Finlan et al. | |
| 5,055,265 A | 10/1991 | Finlan | |
| 5,057,560 A | 10/1991 | Mueller | |
| 5,063,081 A | 11/1991 | Cozzette et al. | |
| 5,064,619 A | 11/1991 | Finlan | |
| 5,076,094 A | 12/1991 | Frye et al. | |
| 5,089,387 A | 2/1992 | Tsay et al. | |
| 5,096,671 A | 3/1992 | Kane et al. | |
| 5,114,676 A | 5/1992 | Leiner et al. | |
| 5,124,254 A | 6/1992 | Hewlins et al. | |
| 5,134,057 A | 7/1992 | Kuypers et al. | |
| 5,137,609 A | 8/1992 | Manian et al. | |
| 5,143,854 A | 9/1992 | Pirrung et al. | |
| 5,152,758 A | 10/1992 | Kaetsu et al. | |
| 5,155,791 A | 10/1992 | Hsiung | |
| 5,182,135 A | 1/1993 | Giesecke et al. | |
| 5,189,902 A | 3/1993 | Groeninger | |
| 5,196,350 A | 3/1993 | Backman et al. | |
| 5,225,935 A | 7/1993 | Watanabe et al. | |
| 5,235,238 A | 8/1993 | Nomura et al. | |
| 5,238,815 A | 8/1993 | Higo et al. | |
| 5,242,828 A | 9/1993 | Bergstrom et al. | |
| 5,262,299 A | 11/1993 | Evangelista et al. | |
| 5,268,306 A | 12/1993 | Berger et al. | |
| 5,280,548 A | 1/1994 | Atwater et al. | |
| 5,304,293 A | 4/1994 | Tierney et al. | |
| 5,315,436 A | 5/1994 | Lowenhar et al. | |
| 5,321,492 A | 6/1994 | Detwiler et al. | |
| 5,327,225 A | 7/1994 | Bender et al. | |
| 5,334,303 A | 8/1994 | Muramatsu et al. | |
| 5,352,582 A | 10/1994 | Lichtenwalter et al. | |
| 5,369,717 A | 11/1994 | Attridge | |
| 5,374,563 A | 12/1994 | Maule | |
| 5,376,255 A | 12/1994 | Gumbrecht et al. | |
| 5,378,638 A | 1/1995 | Deeg et al. | |
| 5,389,534 A | 2/1995 | von Gentzkow et al. | |
| 5,402,075 A | 3/1995 | Lu et al. | |
| 5,404,756 A | 4/1995 | Briggs et al. | |
| 5,415,842 A | 5/1995 | Maule | |
| 5,418,136 A | 5/1995 | Miller et al. | |
| 5,424,220 A | 6/1995 | Goerlach-Graw et al. | |
| 5,430,815 A | 7/1995 | Shen et al. | |
| 5,436,161 A | 7/1995 | Bergstrom et al. | |
| 5,451,683 A | 9/1995 | Barrett et al. | |
| 5,455,475 A | 10/1995 | Josse et al. | |
| 5,464,741 A | 11/1995 | Hendrix | |
| 5,468,606 A | 11/1995 | Bogart et al. | |
| 5,482,830 A | 1/1996 | Bogart et al. | |
| 5,482,867 A | 1/1996 | Barrett et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,496,701 A | 3/1996 | Pollard-Knight | |
| 5,510,481 A | 4/1996 | Bednarski et al. | |
| 5,510,628 A | 4/1996 | Georger, Jr. et al. | |
| 5,512,131 A | 4/1996 | Kumar et al. | |
| 5,514,501 A | 5/1996 | Tarlov | |
| 5,514,559 A | 5/1996 | Markert-Hahn et al. | |
| 5,516,635 A | 5/1996 | Ekins et al. | |
| 5,518,689 A | 5/1996 | Dosmann et al. | |
| 5,527,711 A | 6/1996 | Tom-Moy et al. | |
| 5,552,272 A | 9/1996 | Bogart | |
| 5,554,541 A | 9/1996 | Malmqvist et al. | |
| 5,569,608 A | 10/1996 | Sommer | |
| 5,573,909 A | 11/1996 | Singer et al. | |
| 5,580,697 A | 12/1996 | Keana et al. | |
| 5,580,921 A | 12/1996 | Stepp et al. | |
| 5,585,279 A | 12/1996 | Davidson | |
| 5,589,401 A | 12/1996 | Hansen et al. | |
| 5,591,581 A | 1/1997 | Massey et al. | |
| 5,599,668 A | 2/1997 | Stimpson et al. | |
| 5,620,850 A | 4/1997 | Bamdad et al. | |
| 5,637,509 A | 6/1997 | Hemmilä et al. | |
| 5,643,681 A | 7/1997 | Voorhees et al. | |
| 5,658,443 A | 8/1997 | Yamamoto et al. | |
| 5,677,196 A | 10/1997 | Herron et al. | |
| 5,731,147 A | 3/1998 | Bard et al. | |
| 5,780,251 A | 7/1998 | Klainer et al. | |
| 5,811,526 A | 9/1998 | Davidson | |
| 5,827,748 A | 10/1998 | Golden | |
| 5,830,762 A | 11/1998 | Weindel | |
| 5,832,165 A | 11/1998 | Reichert et al. | |
| 5,843,692 A | 12/1998 | Phillips et al. | |
| 5,863,740 A | 1/1999 | Kientsch-Engel et al. | |
| 5,910,940 A | 6/1999 | Guerra | |
| 5,922,537 A | 7/1999 | Ewart et al. | |
| 5,922,550 A * | 7/1999 | Everhart et al. | 435/7.21 |
| 5,922,615 A | 7/1999 | Nowakowski et al. | |
| 5,965,305 A | 10/1999 | Ligler et al. | |
| 6,030,840 A | 2/2000 | Mullinax et al. | |
| 6,048,623 A | 4/2000 | Everhart et al. | |
| 6,060,237 A | 5/2000 | Nygren et al. | |
| 6,060,256 A | 5/2000 | Everhart et al. | |
| 6,084,683 A | 7/2000 | Bruno et al. | |
| 6,107,038 A | 8/2000 | Choudhary et al. | |
| 6,113,855 A | 9/2000 | Buechler | |
| 6,136,611 A | 10/2000 | Saaski et al. | |
| 6,171,780 B1 | 1/2001 | Pham et al. | |
| 6,180,288 B1 | 1/2001 | Everhart et al. | |
| 6,182,571 B1 | 2/2001 | Jolliffe et al. | |
| 6,200,820 B1 | 3/2001 | Hansen et al. | |
| 6,203,758 B1 | 3/2001 | Marks et al. | |
| 6,221,579 B1 | 4/2001 | Everhart et al. | |
| 6,287,783 B1 | 9/2001 | Maynard et al. | |
| 6,287,871 B1 | 9/2001 | Herron et al. | |
| 6,297,060 B1 | 10/2001 | Nowakowski et al. | |
| 6,331,438 B1 | 12/2001 | Aylott et al. | |
| 6,362,011 B1 | 3/2002 | Massey et al. | |
| 6,399,397 B1 | 6/2002 | Zarling et al. | |
| 6,411,439 B2 | 6/2002 | Nishikawa | |
| 6,416,952 B1 | 7/2002 | Pirrung et al. | |
| 6,423,465 B1 | 7/2002 | Hawker et al. | |
| 6,436,651 B1 | 8/2002 | Everhart et al. | |
| 6,448,091 B1 | 9/2002 | Massey et al. | |
| 6,455,861 B1 | 9/2002 | Hoyt | |
| 6,468,741 B1 | 10/2002 | Massey et al. | |
| 6,556,299 B1 | 4/2003 | Rushbrooke et al. | |
| 6,573,040 B2 | 6/2003 | Everhart et al. | |
| 6,579,673 B2 | 6/2003 | McGrath et al. | |
| 6,582,930 B1 | 6/2003 | Ponomarev et al. | |
| 6,613,583 B1 | 9/2003 | Richter et al. | |
| 6,653,151 B2 | 11/2003 | Anderson et al. | |
| 6,743,581 B1 | 6/2004 | Vo-Dinh | |
| 6,790,531 B2 | 9/2004 | Fournier | |
| 6,913,884 B2 * | 7/2005 | Stuelpnagel et al. | 435/6 |
| 2002/0028455 A1 | 3/2002 | Laibinis et al. | |
| 2003/0027127 A1 | 2/2003 | Cunningham et al. | |
| 2003/0153010 A1 * | 8/2003 | Orth et al. | 435/7.5 |
| 2004/0058385 A1 | 3/2004 | Abel et al. | |

FOREIGN PATENT DOCUMENTS

| | | |
|---|---|---|
| EP | 0420053 A1 | 4/1991 |
| EP | 0453820 A2 | 10/1991 |
| EP | 0453820 A3 | 10/1991 |

| | | |
|---|---|---|
| EP | 0453820 B1 | 10/1991 |
| EP | 0539035 A2 | 4/1993 |
| EP | 0539035 B1 | 4/1993 |
| EP | 0596421 A1 | 5/1994 |
| EP | 0657737 A2 | 6/1995 |
| EP | 0657737 A3 | 6/1995 |
| EP | 1566627 A1 | 8/2005 |
| GB | 2273772 | 6/1994 |
| WO | 9005305 | 5/1990 |
| WO | 9105999 | 5/1991 |
| WO | WO 9113998 A1 | 9/1991 |
| WO | WO 9301308 A1 | 1/1993 |
| WO | WO 9413835 A1 | 6/1994 |
| WO | 9415193 | 7/1994 |
| WO | WO 9609532 A1 | 3/1996 |
| WO | 9615193 | 5/1996 |
| WO | WO 9612962 A1 | 5/1996 |
| WO | 9626435 | 8/1996 |
| WO | WO 9624062 A1 | 8/1996 |
| WO | 9629629 | 9/1996 |
| WO | 9633971 | 10/1996 |
| WO | 9810334 | 3/1998 |
| WO | WO 9815831 A1 | 4/1998 |
| WO | 9827417 | 6/1998 |
| WO | WO 9910742 A1 | 3/1999 |
| WO | WO 9930131 A1 | 6/1999 |
| WO | WO 9931486 A1 | 6/1999 |
| WO | WO 0050891 A1 | 8/2000 |
| WO | WO 0171322 A2 | 9/2001 |
| WO | WO 0181921 A2 | 11/2001 |
| WO | WO 0181921 A3 | 11/2001 |

OTHER PUBLICATIONS

*A Fill-and-Flow Biosensor*, Gooding et al, Analytical Chemistry, vol. 70, No. 15, Aug. 1, 1999, pp. 3131-3136.
A New Tetradentate B-Diketonate-Europium Chelate That Can Be Covalently Bound to Proteins for Time-Resolved Fluoroimmunoassay, Jingli Yuan and Kazuko Matsumoto, Analytical Chemistry, vol. 70, No. 3, Feb. 1, 1998, pp. 596-601.
Abstract of Japanese Patent No. JP2085755.
Abstract of Japanese Patent No. JP2140702.
Abstract of Japanese Patent No. JP2165933.
Abstract of Japanese Patent No. JP2210302.
Abstract of Japanese Patent No. JP5132640.
Abstract of Japanese Patent No. JP8062214.
Phosphorescent Porphyrin Probes in Biosensors and Sensitive Bioassays, D. B. Papkovsky, T. O'Riordan, and A. Soini, Biochemical Society Transactions, vol. 28, Part 2, 2000, pp. 74-77.
Chromophore-Assisted Laser Inactivation of Proteins is Mediated by the Photogeneration of Free Radicals, Joseph C. Liao, Johann Roider, and Daniel G. Jay, Proc. Natl. Acad. Sci. USA, vol. 91, Mar. 1994, pp. 2659-2663.
Diffraction-Based Cell Detection Using a Microcontact Printed Antibody Grating, St. John et al., Analytical Chemistry, vol. 70, No. 6, Mar. 15, 1998, pp. 1108-1111.
Direct Observation of Streptavidin Specifically Adsorbed on Biotin-Functionalized Self-Assembled Monolayers With the Scanning Tunneling Microscope; Angew Chem. Int. Ed. Engl. 30 (1991) No. 5.
Europium Chelate Labels in Time-Resolved Fluorescence Immunoassays and DNA Hybridization Assays, Eleftherios P. Diamandis and Theodore K. Christopoulos, Analytical Chemistry, vol. 62, No. 22, Nov. 15, 1990, pp. 1149-1157.
Evaluation of a Time-Resolved Fluorescence Microscope Using a Phosphorescent PT-Porphine Model System, E.J. Hennink, R. De Haas, N. P. Verwoerd, and H.J. Tanke, Cytometry, vol. 24, 1996, pp. 312-320.
Fabrication of Patterned Electrically Conducting Polypyrrole Using a Self-Assembled Monolayer: A Route to All-Organic Circuits, Gorman, et al., Chem. Mater., vol. 7, 1995, pp. 526-529.
Immunoaffinity Based Phosphorescent Sensor Platform for the Detection of Bacterial Spores, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Inert Phorphorescent Nanospheres as Markers for Optical Assays, Jens M. Kürner, Ingo Klimant, Christian Krause, Harald Preu, Werner Kunz, and Otto S. Wolfbeis, Bioconjugate Chem., vol. 12, 2001, pp. 883-889.
Laser-Mediated Protein Inactivation for Target Validation, Jens Niewöhner, Susanne Rubenwolf, Elisabeth Meyer, and Fritz Rudert, Jul./Aug. 2001, pp. 28-33.
Latex Immunoassay, Leigh B. Bangs, Journal of Clinical Immunoassay, vol. 13, No. 3, 1990, pp. 127-131.
Longwave Luminescent Porphyrin Probes, Dmitry B. Papkovsky, Gelii V. Ponomarev, and Otto S. Wolfbeis, Spectrochimica Acta Part A, vol. 52, 1996, pp. 1629-1638.
Microcontact Printing of Octadecylsiloxane on the Surface of Silicon Dioxide and its Application in Microfabrication, Xia et al., Journal of the American Chemical Society, vol. 117, Sep. 20, 1995, pp. 9576-9577.
Near Infrared Phosphorescent Metalloporphyrins, Alexander P. Savitsky, Anna V. Savitskaja, Eugeny A. Lukjanetz, Svetlana N. Dashkevich, and Elena A. Makaroa, SPIE, vol. 2980, pp. 352-357.
One-Step All-in-One Dry Reagent Immunoassays With Fluorescent Europium Chelate Label and Time-Resolved Fluorometry, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196.1201.
Oxidation of Self-Assembled Monolayers by UV Light With a Wavelenght of 254 Nm, Brewer et al., J. AM. Chem. Soc., vol. 123, 2001, pp. 4089-4090.
Patterning Self-Assembled Monolayers Using Microcontact Printing: A New Technology for Biosensors, Mrksich et al., TIBTECH, vol. 13, No. 6, Jun. 1995, pp. 228-235.
PCT Search Report for PCT/US03/11757.
PCT Search Report for PCT/US03/11757.
PCT Search Report for PCT/US03/29005.
Performance Evaluation of the Phosporescent Porphyrin Label: Solid-Phase Immunoassay of A-Fetoprotein, Tomás C. O'Riordan, Aleksi E. Soini, Juhani T. Soini, and Dmitri B. Papkovsky, Analytical Chemistry, Vo. 74, No. 22, Nov. 15, 2002, pp. 5845-5850.
Photopatterning and Selective Electroless Metallization of Surface Attached Ligands, Dressick, et al., Chemistry of Materials, vol. 5, No. 2, 1993, pp. 148-150.
Polymer Based Lanthanide Luminescent Sensors for the Detection of Nerve Agents, Amanda L. Jenkins, O. Manuel Uy, and George M. Murray, Analytical Communications, vol. 34, Aug. 1997, pp. 221-224.

* cited by examiner

METHOD FOR PRODUCING BIOMOLECULE DIAGNOSTIC DEVICES

PRIORITY INFORMATION

The present application claim priority to and is a divisional application of U.S. application Ser. No. 10/139,025 filed on May 3, 2002 of Cohen, et al., now U.S. Pat. No. 7,771,922, which is incorporated by reference herein.

TECHNICAL FIELD OF THE INVENTION

The present invention relates generally to the field of detecting analytes in a medium, and more particularly to a process for preparing analyte-specific diagnostic sensors to indicate the presence of the analyte in a medium in, for example, a diffraction/holography format.

BACKGROUND

There are many systems and devices available for detecting a wide variety of analytes in various media. Many of the prior systems and devices are, however, relatively expensive and require a trained technician to perform the test. A need has been recognized in the art for biosensor systems that are easy and inexpensive to manufacture, and capable of reliable and sensitive detection of analytes. Reference is made, for example, to U.S. Pat. Nos. 5,922,550; 6,060,256; and 6,221,579 B1.

Various advances have been made in the industry for producing biosensors. For example, U.S. Pat. No. 5,512,131 to Kumar, et al., describes a device that includes a polymer substrate having a metal coating. An analyte specific receptor layer is stamped onto the coated substrate. A diffraction pattern is generated when an analyte binds to the device. A visualization device, such as a spectrometer, is then used to determine the presence of the diffraction pattern. A drawback to this type of device is, however, the fact that the diffraction pattern is not discernible by the naked eye and, thus, a complex visualization device is needed to view the diffraction pattern. Also, the device is generally not able to detect smaller analytes that do not produce a noticeable diffraction pattern.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color. The second color is exhibited in response to the same light when the analyte is present on the surface. The change from one color to another can be measured either by use of an instrument, or by the naked eye. A drawback with the device is, however, the relatively high cost of the device and problems associated with controlling the various layers that are placed on the wafer substrate.

Contact printing techniques have been explored for producing biosensors having a self-assembling monolayer. U.S. Pat. No. 5,922,550 describes a biosensor having a metalized film upon which is printed (contact printed) a specific predetermined pattern of an analyte-specific receptor. The receptor materials are bound to the self-assembling monolayer and are specific for a particular analyte or class of analytes. Attachment of a target analyte that is capable of scattering light to select areas of the metalized plastic film upon which the receptor is printed causes diffraction of transmitted and/or reflected light. A diffraction image is produced that can be easily seen with the eye or, optionally, with a sensing device.

U.S. Pat. No. 6,060,256 describes a similar device having a metalized film upon which is printed a specific predetermined pattern of analyte-specific receptor. The '256 patent is not limited to self-assembling monolayers, but teaches that any receptor which can be chemically coupled to a surface can be used. The invention of the '256 patent uses methods of contact printing of patterned monolayers utilizing derivatives of binders for microorganisms. One example of such a derivative is a thiol. The desired binding agent can be thiolated antibodies or antibody fragments, proteins, nucleic acids, sugars, carbohydrates, or any other functionality capable of binding an analyte. The derivatives are chemically bonded to metal surfaces such as metalized polymer films, for example via a thiol.

A potential issue of the contact printing techniques described above for producing diffraction-based biosensors is the possibility of contamination from the print surface (i.e., stamp) during the printing process. Also, there is the possibility of uneven application or inking of the substances due to pressure and contact variations inherent in the process, as well as surface energy variations.

The present invention relates to a biosensor system that is easy and inexpensive to manufacture, is capable of reliable and sensitive detection of analytes, and avoids possible drawbacks of conventional microcontact printing techniques.

SUMMARY OF THE INVENTION

Objects and advantages of the invention will be set forth in part in the following description, or may be obvious from the description, or may be learned through practice of the invention.

The present invention provides a relatively inexpensive yet sensitive biosensor device, a method for producing such biosensor devices, and a method for detecting analytes of interest present in a medium.

The biosensor includes a substrate upon which a layer containing a bifunctional crosslinking agent is applied in a light protected environment generally uniformly over an entire surface of the substrate member. This agent has a molecular make-up such that one side of the molecule reacts with and forms a relatively strong bond with the substrate member. The other end of the agent has a photo-reactive group such that, in the presence of or after exposure to an irradiating energy source of sufficient amplitude and frequency, the agent cross-links with any other molecules in close proximity. Examples of such bifunctional crosslinking agents include SANPAH (N-Succinimidyl 2-[p-azido-salicylamido]ethyl-1,3'-dithiiopropionate); SAND (Sulfosuccinimidyl 2-[m-azido-o-nitro-benzamido]ethyl-1,3'-dithiopropionate); and ANB-NOS (N-5-Azido-2-nitrobenzoyloxysuccinimide).

The substrate may be any one of a wide variety of suitable materials, including plastics, metal coated plastics and glass, functionalized plastics and glass, silicon wafers, foils, glass, etc. Desirably, the substrate is flexible, such as a polymeric film, in order to facilitate the manufacturing process.

The crosslinking agent layer is desirably applied in a light-protected environment by any number of known techniques, including dipping, spraying, rolling, spin coating and any other technique wherein the layer can be applied generally uniformly over the entire test surface of the substrate. The invention also includes contact printing methods of applying the photo-reactive crosslinking agent layer.

In one embodiment, a layer containing a receptive material (e.g., biomolecules) is then applied over the photo-reactive crosslinking agent, desirably in a light protected environment. The receptive material is selected so as to have a particular affinity for an analyte of interest. The receptive material layer may be applied by any number of known techniques, including dipping, spraying, rolling, spin coating and any other technique wherein the layer can be applied generally uniformly over the entire test surface of the substrate. The invention also includes contact printing methods of applying the receptive material layer, as long as such methods are conducted in a manner to prevent inconsistent inking and contamination from contact during the initial coating process.

A mask having a pattern of exposed and shielded areas is placed over the substrate. The mask may include any desired pattern of protected or shielded areas and exposed areas (e.g., transparent or translucent areas, as well as holes or openings in the mask structure). The exposed areas of the mask will correspond to a pattern of active receptive material areas (biomolecules) and the shielded areas of the mask will define a pattern of inactive blocking material areas. The mask and substrate combination is then irradiated with an energy source sufficient to activate the crosslinking agent such that the photo-reactive groups crosslink or attach to the biomolecules in the exposed areas of the mask and thus "secure" the biomolecules relative to the substrate in the exposed areas.

In a light protected environment, the mask is removed and the unattached biomolecules that were underlying the shielded areas of the mask are removed from the substrate member by, for example, a washing or rinsing procedure. The crosslinked biomolecules remain attached to the substrate member in a pattern corresponding to the exposed areas of the mask.

In one embodiment, desirably in a light protected environment, a material containing molecules different than the biomolecules selected for the analyte of interest is applied to the substrate member. These "different" molecules will serve, in essence, to fill in or block the regions on the substrate between the active receptive material areas and may be, for example, biomolecules that specifically do not have an affinity for the analyte of interest. In general, any type of blocking molecule may be used for this purpose.

The substrate member is then exposed again to the energy source for a sufficient time to activate the photo-reactive groups of the crosslinking agent. The blocking molecules become crosslinked or attached to the substrate member in a pattern corresponding to the originally shielded areas of the mask.

The substrate member is finally washed or rinsed to remove any remaining unattached blocking molecules. A patterned monolayer of defined areas of active biomolecules for an analyte of interest interposed between areas of blocking molecules remains on the substrate.

In an alternative embodiment, the blocking material may be first applied to the crosslinking agent and exposed through a mask. The receptive material would then be applied after the masking process. Thus, in this embodiment, the pattern of active receptive material areas corresponds to the shielded areas of the mask, and the pattern of inactive blocking material areas corresponds to the exposed areas of the mask.

It should be appreciated that the invention is not limited to any particular pattern defined by the mask. Virtually any number and combination of exposed shapes or openings are possible. In one particular embodiment, the pattern is defined by about 10 micron diameter pixels at a spacing of about 5 microns over the test surface of the substrate.

The photo-reactive crosslinking agent is irradiated with an energy source selected particularly for activating the specific type of photo-reactive agent. The invention is not limited to any particular energy source. For example, the energy source may be a light source, e.g., an ultraviolet (UV) light source, an electron beam, a radiation source, etc. Care should be taken such that the exposure is sufficient for activating the crosslinking agent, but does not destroy or break down the receptive material or does not damage the underlying substrate member. Upon subsequent exposure of the biosensor to a medium containing an analyte of interest, the analyte binds to the biomolecules in the active areas. The biosensor will then diffract transmitted light in a diffraction pattern corresponding to the active areas. The diffraction pattern may be visible to the naked eye or, optionally, viewed with a sensing device.

In the case where an analyte does not scatter visible light because the analyte is too small or does not have an appreciable refractive index difference compared to the surrounding medium, a diffraction-enhancing element, such as polymer microparticles, may be used. These micorparticles are coated with a binder or receptive material that also specifically binds to the analyte. Upon subsequent coupling of the analyte to both the patterned biomolecules in the receptive material layer as well as the microparticles, a diffraction image is produced which can be easily seen with the eye or, optionally, with a sensing device.

By "diffraction" it is meant the phenomenon, observed when waves are obstructed by obstacles, of the disturbance spreading beyond the limits of the geometrical shadow of the object. The effect is marked when the size of the object is of the same order as the wavelength of the waves. In the present invention, the obstacles are analytes (with or without or attached microparticles) and the waves are light waves.

In another embodiment of the present invention, nutrients or receptors for a specific class of microorganisms can be incorporated as the receptive material in the active areas. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern.

The present invention provides a low-cost, disposable biosensor that can be mass produced. The biosensors of the present invention can be produced as a single test for detecting an analyte or it can be formatted as a multiple test device. The uses for the biosensors of the present invention include, but are not limited to, detection of chemical or biological contamination in garments, such as diapers, the detection of contamination by microorganisms in prepacked foods such as meats, fruit juices or other beverages, and the use of the biosensors of the present invention in health diagnostic applications such as diagnostic kits for the detection of proteins, hormones, antigens, nucleic acids, microorganisms, and blood constituents. It should be appreciated that the present invention is not limited to any particular use or application.

These and other features and advantages of the present invention will become apparent after a review of the following detailed description of the disclosed embodiments.

DETAILED DESCRIPTION

Figure 1:
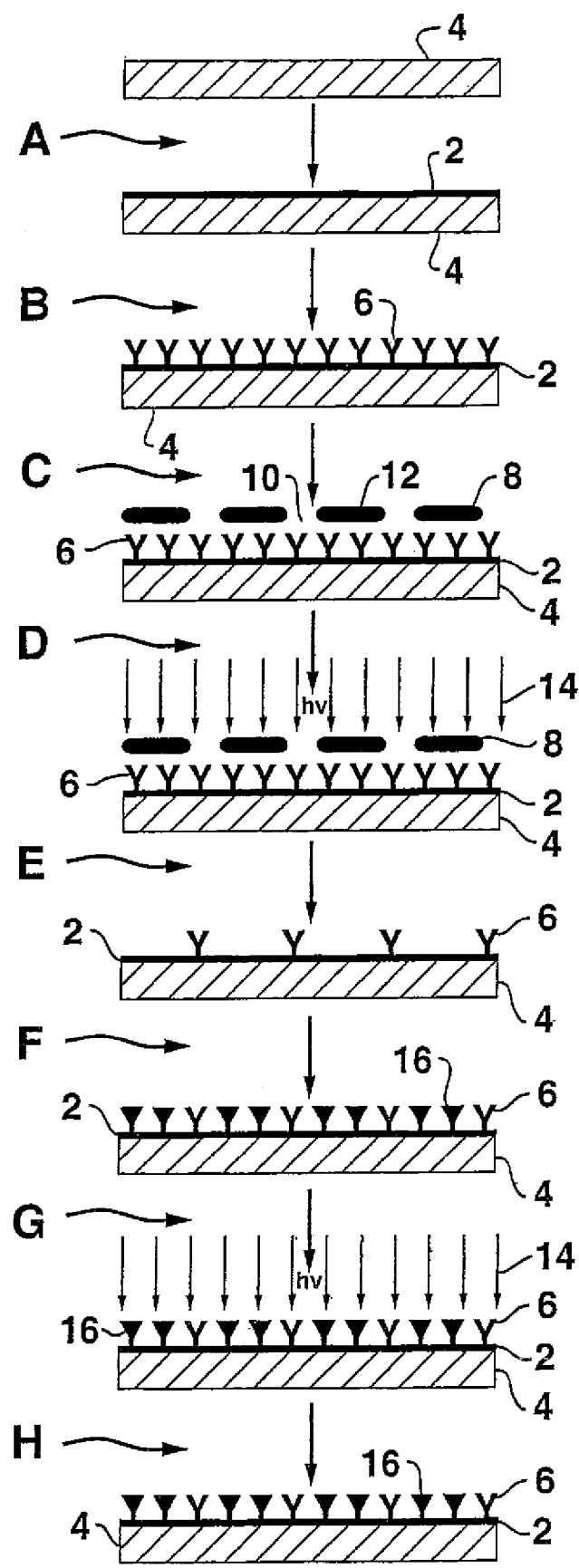
FIG. 1 is a schematic representation of a method for producing biosensors according to the invention by a masking process.

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention include these and other modifications and variations as come within the scope and spirit of the invention.

The present invention features improved biosensing devices, and methods for using such biosensing devices, for detecting and quantifying the presence or amount of an analyte of interest within a medium. The analytes that can be detected by the present invention include, but are not limited to, microorganisms such as bacteria, yeasts, fungi, viruses, proteins, nucleic acids, and small molecules. The biosensing devices according to the invention are relatively inexpensive and have advantages over conventional micro-contact printed biosensors.

The present invention comprises, in broad terms, a process of defining an active pattern of analyte-specific receptive material on a substrate surface by photo-masking the substrate. A layer containing a photo-reactive crosslinking agent is first applied to a surface of the substrate member. The molecular structure of the crosslinking agent is such that one functional group or side thereof reacts with or attaches to the surface of the substrate member. Another functional group or side of the crosslinking agent is photoactivatable such that, in the presence of the correct amplitude and frequency of electromagnetic radiation, the group will cross-link with other molecules in close proximity. Specifically, the photo-reactive crosslinking agent may be any one of a number of substances, including SANPAH (N-Succinimidyl 2-[p-azido-salicylamido]ethyl-1,3'-dithiiopropionate); SAND (Sulfosuccinimidyl 2-[m-azido-o-nitro-benzamido]ethyl-1,3'-dithiopropionate); and ANB-NOS (N-5-Azido-2-nitrobenzoyloxysuccinimide).

A generally uniform coating of the receptive material or the blocking material is then applied to the substrate surface over the crosslinking agent layer. A mask is placed over the substrate, and the mask and substrate combination is irradiated with an energy source specifically selected to activate the photo-reactive group of the crosslinking agent. In its basic form, the "mask" serves to shield at least one area or section of the substrate member from the irradiating energy source and to expose at least one adjacent section to the energy source. For example, the mask may be a generally transparent or translucent blank (e.g., a strip of material) having any pattern of shielded regions printed or otherwise defined thereon. The exposed unshielded regions of the mask correspond to the exposed areas of the substrate member. Alternatively, the mask may simply be a single object placed upon the substrate. The area under the object would be shielded and thus define an active area of the receptive material, and the area around the object would be exposed to the energy source and thus define an area of inactive receptive material. Alternatively, the object may have any pattern of openings defined therethrough corresponding to the exposed areas.

As mentioned, the energy source is selected so that the reactive group of the exposed crosslinking agent is activated and thus attaches or crosslinks with the overlying material (the receptive material or blocking material). The photo-reactive agent in the regions shielded by the mask remains "unactivated." Thus, upon removal of the mask, a pattern of either active receptive material or blocking material is defined on the substrate member corresponding to the pattern of the exposed areas of the mask. It should be understood that "pattern" includes as few as one active area and one inactive area.

The receptive material or blocking material that was under the shielded areas of the mask (and thus not crosslinked with the crosslinking agent) is removed from the substrate in any suitable cleansing process, such as rinsing the substrate with water or a buffer solution.

A generally uniform layer of the respective other material is then applied to the substrate member. For example, if the receptive material was applied to the substrate before the masking process, the blocking material is subsequently applied. Likewise, if the blocking material was first applied, the receptive material is subsequently applied. The substrate member is then exposed to the energy source a second time so as to activate the remaining crosslinking agent in the areas of the substrate member that were shielded by the mask in the masking process. Exposure is sufficient to activate the agent without damaging or deactivating the receptive material (if the receptive material was applied first). During or after exposure to the energy source, the remaining crosslinking agent is activated and, thus, a pattern of the other material (blocking material or receptive material) is defined on substrate member corresponding to the pattern of the shielded areas of the mask. Any remaining un-linked material is then cleaned from the substrate member in an appropriate cleaning process, e.g., a rinsing step.

Upon subsequent exposure of the biosensor to a medium containing the analyte of interest, such analyte will bind to the biomolecules in the active receptive material areas. The analyte results in diffraction of transmitted and/or reflected light in a visible diffraction pattern corresponding to the active receptive material areas. As discussed in greater detail below, an enhancer may be used for enhancing diffraction from extremely small analytes.

The analytes that are contemplated as being detected using the present invention include, but are not limited to, bacteria; yeasts; fungi; viruses; rheumatoid factor; antibodies, including, but not limited to IgG, IgM, IgA, IgD, and IgE antibodies; carcinoembryonic antigen; streptococcus Group A antigen; viral antigens; antigens associated with autoimmune disease; PSA (prostate specific antigen) and CRP (C-reactive protein) antigens; allergens; tumor antigens; streptococcus Group B antigen; HIV I or HIV II antigen; or host response (antibodies) to these and other viruses; antigens specific to RSV or host response (antibodies) to the virus; antigen; enzyme; hormone; polysaccharide; protein; lipid; carbohydrate; drug or nucleic acid; *Salmonella* species; *Candida* species, including, but not limited to *Candida albicans* and *Candida tropicalis; Neisseria meningitides* groups A, B, C, Y and W sub 135, *Streptococcus pneumoniae; E. coli; Haemophilus influenza* type A/B; an antigen derived from microorganisms; a hapten; a drug of abuse; a therapeutic drug; an environmental agent; and antigens specific to Hepatitis. In broad terms, the "analyte of interest" may be thought of as any agent whose presence or absence from a biological sample is indicative of a particular health state or condition.

It is also contemplated that nutrients for a specific class of microorganism can be incorporated into the receptive material layer. In this way, very low concentrations of microorganisms can be detected by exposing the biosensor of the present invention with the nutrients incorporated therein to the suspect medium and then incubating the biosensor under conditions appropriate for the growth of the bound microorganism. The microorganisms are allowed to grow until there are enough organisms to form a diffraction pattern. Of course, in some cases, the microorganism is present or can multiply enough to form a diffraction pattern without the presence of a nutrient in the active receptive material areas.

The receptive material is characterized by an ability to specifically bind the analyte or analytes of interest. The variety of materials that can be used as receptive material is limited only by the types of material which will combine selectively (with respect to any chosen sample) with a secondary partner. Subclasses of materials which fall in the overall class of receptive materials include toxins, antibodies, antibody fragments, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, aptamers, peptides, and any other member of a specific binding pair. This list only incorporates some of the many different materials that can be coated onto the substrate surface to produce a thin film assay system. Whatever the selected analyte of interest is, the receptive material is designed to bind specifically with the analyte of interest.

The blocking material may be any material that specifically does not bind the analyte of interest. The blocking material may be a passive material, such as milk proteins such as beta casein, albumin such as bovine serum albumin, and other proteins that do not recognize the target analyte; polymers such as polyvinyl pyrolidone, polyethylene glycol, and/or polyvinyl alcohol; surfactants (e.g., Pluronics), carbohydrates, antibodies, DNA, PNA, ubiquitin, and streptavidin. In other embodiments, the blocking material may be a receptive material that binds only with analytes different from the analyte of interest.

The matrix or medium containing the analyte of interest may be a liquid, a solid, or a gas, and can include a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material. For example, receptive material for bacteria may specifically bind a surface membrane component, protein or lipid, a polysaccharide, a nucleic acid, or an enzyme. The analyte which is specific to the bacteria may be a polysaccharide, an enzyme, a nucleic acid, a membrane component, or an antibody produced by the host in response to the bacteria. The presence or absence of the analyte may indicate an infectious disease (bacterial or viral), cancer or other metabolic disorder or condition. The presence or absence of the analyte may be an indication of food poisoning or other toxic exposure. The analyte may indicate drug abuse or may monitor levels of therapeutic agents.

One of the most commonly encountered assay protocols for which this technology can be utilized is an immunoassay. However, the general considerations apply to nucleic acid probes, enzyme/substrate, and other ligand/receptor assay formats. For immunoassays, an antibody may serve as the receptive material or it may be the analyte of interest. The receptive material, for example an antibody or an antigen, should form a stable, reactive layer on the substrate surface of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface, a decrease in the amount of receptive material on the test surface, or a change in refractive index. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptive material occurs is not important to this invention, but may impact the reaction conditions used in the final assay protocol.

In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern becomes discernible in less than one hour after contact of the analyte with the biosensing device of the present invention.

The diffraction grating which produces the diffraction of light upon interaction with the analyte must have a minimum periodicity of about ½ the wavelength and a refractive index different from that of the surrounding medium. Very small analytes, such as viruses or molecules, can be detected indirectly by using a larger, "diffraction-enhancing element," such as a micro-particle, that is specific for the small analyte. One embodiment in which the small analyte can be detected comprises coating the enhancing particle, such as a latex bead or polystyrene bead, with a receptive material, such as an antibody, that specifically binds to the analyte of interest. Particles that can be used in the present invention include, but are not limited to, glass, cellulose, synthetic polymers or plastics, latex, polystyrene, polycarbonate, proteins, bacterial or fungal cells, silica, cellulose acetate, carbon, and the like. The particles are desirably spherical in shape, but the structural and spatial configuration of the particles is not critical to the present invention. For instance, the particles could be slivers, ellipsoids, cubes, random shape and the like. A desirable particle size ranges from a diameter of approximately 0.1 micron to 50 microns, desirably between approximately 0.1 micron and 2.0 microns. The composition of the particle is not critical to the present invention.

Desirably, the receptive material layer on the substrate will specifically bind to an epitope on the analyte that is different from the epitope used in the binding to the enhancing particle. Thus, for detecting a small analyte in a medium, the medium is first exposed to the latex particles having the virus-specific receptive material thereon. The small analytes of interest in the medium will bind to the latex particles. Then, the latex particles are optionally washed and exposed to the biosensor film with the pattern of active receptive material areas containing the virus-specific antibodies. The antibodies then bind to the viral particles on the latex bead thereby immobilizing the latex beads in the same pattern as the active areas on the film. Because the bound latex beads will cause diffraction of the visible light, a diffraction pattern is formed, indicating the presence of the viral particle in the liquid. Other combinations using diffraction enhancing particles are described, for example, in U.S. Pat. No. 6,221,579 incorporated herein for all purposes.

Any one of a wide variety of materials may serve as the substrate to which the receptive material and blocking material are applied. Such materials are well known to those skilled in the art. For example, the substrate may be formed of any one of a number of suitable plastics, metal coated plastics and glass, functionalized plastics and glass, silicon wafers, glass, foils, etc. Rather than requiring a rigid substrate for the photopatterning process described herein, it has been found that thermoplastic films are quite suitable. Such films include, but are not limited to, polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80 percent. Other suitable thermoplastics and suppliers may be found, for example, in reference works such as the Modern Plastics Encyclopedia (McGraw-Hill Publishing Co., New York 1923-1996).

In one embodiment of the invention, the thermoplastic film may have a metal coating. The film with metal coating thereon may have an optical transparency of between approximately 5 percent and 95 percent. A more desired optical transparency for the thermoplastic film used in the present invention is between approximately 20 percent and 80 percent. In a desired embodiment of the present invention, the thermoplastic film has at least an approximately 80 percent optical transparency, and the thickness of the metal coating is such as to maintain an optical transparency greater than about 20 percent, so that diffraction patterns can be produced by either reflected or transmitted light. This corresponds to a metal coating thickness of about 20 nanometers. However, in other embodiments of the invention, the metal thickness may be between approximately 1 nanometer and 1000 nanometers.

The preferred metal for deposition on the film is gold. However, silver, aluminum, chromium, copper, iron, zirconium, platinum, nickel, and titanium, as well as oxides of these metals, may be used. Chromium oxide can be used to make metalized layers.

The receptive material and blocking material may be applied to the substrate over the photo-reactive crosslinking agent by any conventional method. The material is applied so that it generally uniformly covers an entire (for example, upper) surface of the substrate. Non-contact methods for applying the materials may be desired so as to eliminate the possibility of contamination by contact during application. Suitable application methods include, but are not limited to, dipping, spraying, rolling, spin coating, and any other technique wherein the receptive material layer can be applied generally uniformly over the entire test surface of the substrate. Simple physisorption can occur on many materials, such as polystyrene, glass, nylon, metals, polycarbonate, or other materials well known to those skilled in the art. One particular embodiment of immobilizing the analyte-specific receptive material layer involves molecular attachment, such as that possible between thiol or disulfide-containing compounds and gold. Typically, a gold coating of about 5 to about 2000 nanometers thick is supported on a silicon wafer, glass, or polymer film (such as a MYLAR® film). The analyte-specific receptor attaches to the gold surface upon exposure of a solution of the receptive material.

Although not preferred, the invention also includes contact printing methods of applying the materials. The technique selected should minimize the amount of receptive material required for coating a large number of test surfaces and maintain the stability/functionality of the receptive material during application. The technique should also apply or adhere the receptive material to the substrate in a uniform and reproducible fashion.

It is also contemplated that the receptive material layer may be formed on the substrate as a self-assembling monolayers of alkanethiolates, carboxylic acids, hydroxamic acids, and phosphonic acids on metalized thermoplastic films. The self-assembling monolayers have receptive material bound thereto. Reference is made to U.S. Pat. No. 5,922,550 for a more detailed description of such self-assembling monolayers and methods for producing the monolayers. The '550 patent is incorporated herein in its entirety for all purposes.

The mask may be formed of any suitable material that shields the underlying portion of the substrate from the irradiating energy source. A material that has proven useful for defining patterns of active and inactive receptive material regions on a gold-plated MYLAR® film coated with an antibody solution is a transparent or translucent polymer film (such as MYLAR®) having a pattern of shielded regions printed thereon. This type of mask is useful for light sources (irradiating energy source) with a wavelength to greater than or equal to about 330 nanometers. For light sources having a wavelength below about 330 nanometers, a quartz or fused silica mask having chrome or other metal plated blocked regions defined thereon may be used. It may be desired to select a hole pattern and size so as to maximize the visible diffraction contrast between the active and inactive regions. It has been found suitable if the active regions are defined as generally circular with a diameter of about 10 microns and spaced from each other by about 5 microns.

Any suitable energy source may be selected for irradiating the mask and substrate combination. An energy source is selected particularly for activating the specific type of photo-reactive crosslinking agent. The energy source may be, for example, a light source, e.g., an ultraviolet (UV) light source, an electron beam, a radiation source, etc. In one particular embodiment, the photo-reactive crosslinking agent is SANPAH and the activating energy source is a UV light source. The sensor is exposed to the light source for a period of time sufficient for the photo-reactive group of the crosslinking agent to be activated and thus link or bind with either the receptive material or blocking material. It should be appreciated that the invention is not limited to any particular type of light or activating energy source or exposure times. The type of light (e.g., wavelength) and exposure times may vary depending on the particular type of photo-reactive crosslinking agent. Other suitable energy sources may include tuned lasers, electron beams, various types of radiation beams including gamma and X-ray sources, various intensities and wavelengths of light including light beams of sufficient magnitude at the microwave and below wavelengths, etc. Care should be taken that the energy source does not damage (e.g., melt) the underlying substrate or mask.

FIG. 1 is a schematic representation of one method for producing biosensors according to the invention. In this example, the receptive material is applied first prior to the masking process such that the pattern of receptive material areas corresponds to the pattern of exposed areas in the mask. It should also be understood that the steps are carried out in a controlled light protected environment.

Step A represents the photo-reactive crosslinking agent 2 applied to a substrate member 4. Excess agent may be rinsed or washed from the substrate.

Step B represents the receptive material (biomolecules) layer 6 applied to the substrate member 4 over the crosslinking agent 2.

Step C depicts the mask 8 disposed over the substrate member 4. The mask 8 includes exposed or open regions 10 and shielded regions 12 defined thereon.

Step D represents the mask 8 and substrate member 4 combination being irradiated with an energy source 14. It can be seen that the areas of the substrate member 4 underlying the shielded regions 12 of the mask 8 are protected from the energy source 14. The photo-reactive groups of the crosslinking agent 2 exposed to the energy source 14 through the open regions 10 of the mask 8 are activated by the energy source 14 and link with the biomolecules 6 in the exposed areas. The crosslinking agent 2 underlying the shielded regions 12 of the mask 8 is not exposed to the energy source and is thus unactivated. The biomolecules 6 in these regions are thus not linked or attached with the agent 2 and are removed in a subsequent cleaning (i.e., rinsing) step.

Step E represents the biosensor after the masking process and removal of the unreacted receptive material.

Step F represents the biosensor after a layer of blocking material 16 has been applied to the substrate member 4. The FIGURE depicts the blocking material as separate molecules dispersed between the attached biomolecules 6. However, it should be appreciated that this is for illustrative purposes only. The blocking material would likely be applied as a uniform coating over the entire substrate member.

Step G represents the substrate member being irradiated the second time with the energy source 14 to activate the remaining crosslinking agent 2 in the areas previously shielded by the mask 8. The photo-reactive groups of the crosslinking agent 2 are activated and link with or attach the blocking molecules 16.

Step H represents the biosensor in its final form after cleaning or rinsing of any excess blocking material 16. The biosensor includes a pattern of active areas of the receptive material 6 corresponding to the exposed areas of the mask 8, and a pattern of areas of the blocking material 16 corresponding to the shielded areas of the mask 8.

The biosensors according to the invention have a wide range of uses in any number of fields. The uses for the biosensors of the present invention include, but are not limited to, detection of chemical or biological contamination in garments, such as diapers, generally the detection of contamination by microorganisms in prepacked foods such as meats, fruit juices or other beverages, and the use of the biosensors of the present invention in health diagnostic applications such as diagnostic kits for the detection of proteins, hormones, antigens, nucleic acids, DNA, microorganisms, and blood constituents. The present invention can also be used on contact lenses, eyeglasses, window panes, pharmaceutical vials, solvent containers, water bottles, band-aids, wipes, and the like to detect contamination. In one embodiment, the present invention is contemplated in a dipstick form in which the patterned substrate is mounted at the end of the dipstick. In use the dipstick is dipped into the liquid in which the suspected analyte may be present and allowed to remain for several minutes. The dipstick is then removed and then, either a light is projected through the substrate or the substrate is observed with a light reflected from the substrate. If a diffraction pattern is observed, then the analyte is present in the liquid.

In another embodiment of the present invention, a multiple analyte test is constructed on the same support. A strip may be provided with several patterned substrate sections. Each section has a different receptive material that is different for different analytes. It can be seen that the present invention can be formatted in any array with a variety of patterned substrates thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine whether there is microbial contamination.

It should be understood that the present invention includes various other embodiments, modifications, and equivalents to the examples of the invention described herein which, after reading the description of the invention, may become apparent to those skilled in the art without departing from the scope and spirit of the present invention.

What is claimed is:

1. A method of making a biosensor, comprising the steps of:
    applying a photo-reactive crosslinking agent directly to a surface of a substrate member;
    forming one of a receptive material layer and a blocking material layer over the crosslinking agent;
    placing a mask over the substrate member, the mask having a configuration so as to shield at least one underlying area of the substrate member while exposing at least one adjacent area, and irradiating the substrate member and mask combination with an energy source sufficient to activate the crosslinking agent in the areas exposed by the mask, the activated crosslinking agent crosslinking with the respective receptive material or blocking material in the exposed areas;
    cleaning the unreacted receptive material or blocking material from the shielded areas of the substrate member after removal of the mask;
    forming a layer of the respective other of the blocking material and receptive material over the surface of the substrate member, and irradiating the substrate member with the energy source so as to activate the remaining crosslinking agent in the previously shielded areas, the activated crosslinking agent crosslinking with the respective blocking material or receptive material; and
    wherein a resulting pattern of active receptive material areas and blocking material areas are defined according to the pattern of shielded and exposed areas of the mask.

2. The method as in claim 1, comprising forming the receptive material layer on the substrate before the blocking material layer such that the pattern of active areas of receptive material correspond to the exposed areas of the mask.

3. The method as in claim 1, comprising selecting the substrate member from the group of materials consisting of plastics, metal coated plastics and glass, functionalized plastics and glass, silicon wafers, glass, and foils.

4. The method as in claim 1, wherein the substrate member comprises a polymer film coated with a metal.

5. The method as in claim 4, comprising selecting the metal from the group consisting of gold, silver, chromium, nickel, platinum, aluminum, iron, copper, gold oxide, chromium oxide, titanium, titanium oxide, silicone, silicone oxide, silicone nitride, silver oxide, or zirconium.

6. The method as in claim 1, wherein the receptive material in the active areas facilitates diffraction of transmitted or reflected light in a diffraction pattern corresponding to the active receptive material areas, and further comprising viewing the diffraction pattern of active areas of receptive material with the naked eye.

7. The method as in claim 1, wherein the receptive material is protein based.

8. The method as in claim 6, wherein the receptive material is an antibody.

9. The method as in claim 1, comprising irradiating the substrate member with UV light at a wavelength sufficient for activating the photo-reactive crosslinking agent exposed through the mask.

10. The method as in claim 1, comprising selecting the receptive material from at least one of antigens, antibodies, nucleotides, chelators, enzymes, bacteria, yeasts, fungi, viruses, bacterial pill, bacterial flagellar materials, nucleic acids, polysaccharides, lipids, proteins, carbohydrates, metals, hormones, peptides, aptamers and respective receptors for said materials.

11. The method as in claim 1, wherein the analyte of interest is selected from at least one of a bacteria, yeast, fungus, virus, rheumatoid factor, IgG, IgM, IgA, IgD and IgE antibodies, carcinoembryonic antigen, streptococcus Group A antigen, viral antigens, antigens associated with autoimmune disease, allergens, tumor antigens, streptococcus group B antigen, HIV I or HIV II antigen, antibodies viruses, antigens specific to RSV, an antibody, antigen, enzyme, hormone, polysaccharide, protein, lipid, carbohydrate, drug, nucleic acid, Neisseria meningitides groups A, B, C, Y and W sub 135, *Streptococcus pneumoniae, E. coli* K1, Haemophilus influenza type A/B, an antigen derived from microorganisms, PSA and CRP antigens, a hapten, a drug of abuse, a therapeutic drug, an environmental agents, or antigens specific to Hepatitis.

12. The method as in claim 1, wherein the photo-reactive crosslinking agent is one of SANPAH (N-Succinimidyl 2-[p-azido-salicylamido]ethyl-1,3'-dithiiopropionate); SAND (Sulfosuccinimidyl 2-[m-azido-o-nitro-benzamido]ethyl-1, 3'-dithiopropionate); and ANB-NOS (N-5-Azido-2-nitrobenzoyloxysuccinimide).

* * * * *